Figure 1:
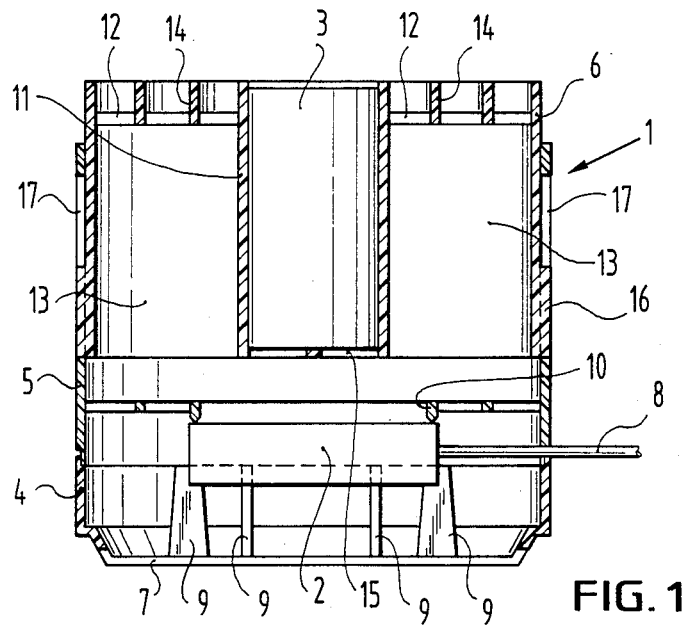
Figure 2:
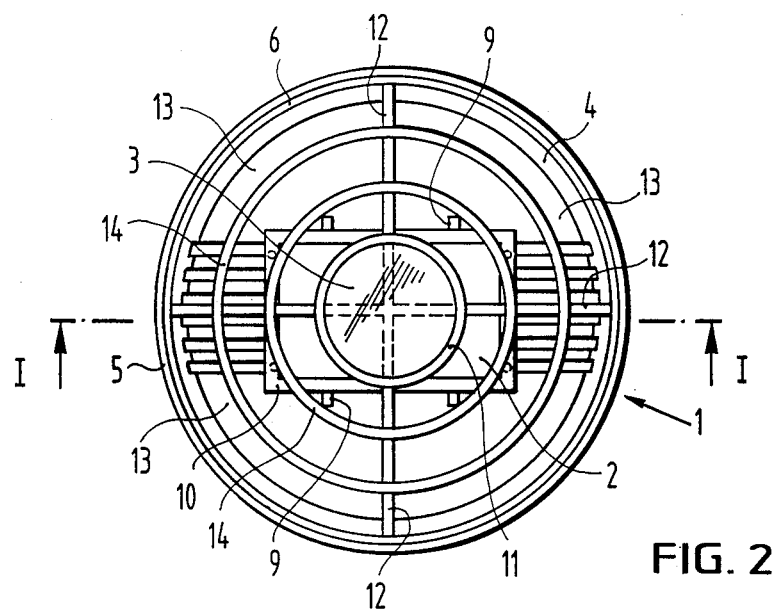
Figure 3:
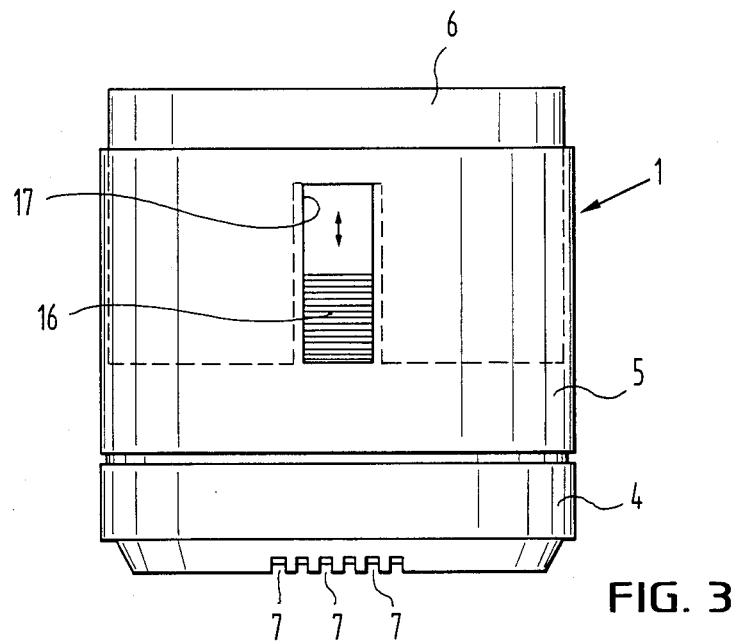
Figure 4:
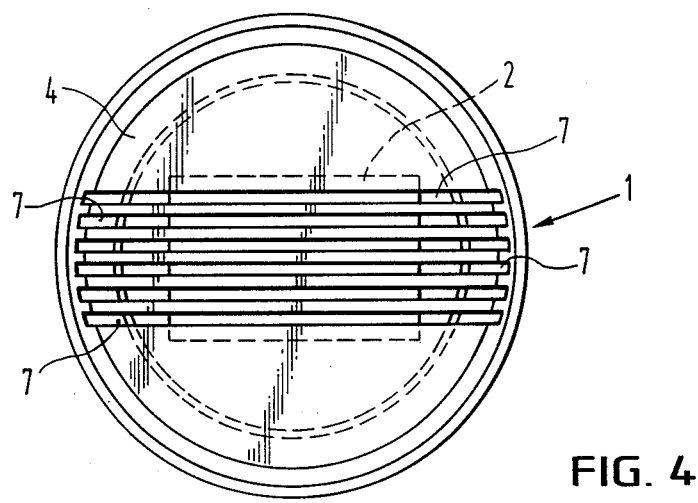

United States Patent [19]

Von Philipp et al.

[11] Patent Number: 4,769,528

[45] Date of Patent: Sep. 6, 1988

[54] APPARATUS FOR THE EVAPORATION OF ACTIVE INGREDIENTS SUCH AS, FOR EXAMPLE, PYRETHRUM, INCORPORATED IN CELLULOSE OR OTHER CARRIER MATERIALS

[75] Inventors: Fritz Von Philipp; Horst Hautmann, both of Neuburg, Fed. Rep. of Germany

[73] Assignee: Globol-Werk GmbH, Neuburg/Donau, Fed. Rep. of Germany

[21] Appl. No.: 923,796

[22] PCT Filed: Dec. 11, 1985

[86] PCT No.: PCT/EP85/00695

§ 371 Date: Sep. 22, 1986

§ 102(e) Date: Sep. 22, 1986

[87] PCT Pub. No.: WO86/04484

PCT Pub. Date: Aug. 14, 1986

[30] Foreign Application Priority Data

Jan. 30, 1985 [DE] Fed. Rep. of Germany ... 8502409[U]

[51] Int. Cl.⁴ .............................................. F22B 1/28
[52] U.S. Cl. ................................... 219/271; 219/275; 118/726
[58] Field of Search ...................... 219/271, 275, 276; 432/262; 118/726

[56] References Cited

U.S. PATENT DOCUMENTS 4,482,799 11/1984 Pricenski et al. ............... 219/271 X
4,543,467 9/1985 Eisele et al. .......................... 219/271

FOREIGN PATENT DOCUMENTS 937866 9/1963 United Kingdom .

*Primary Examiner*—E. A. Goldberg
*Assistant Examiner*—M. M. Lateef
*Attorney, Agent, or Firm*—Townsend & Townsend

[57] ABSTRACT

An apparatus for the evaporation of active ingredients incorporated in cellulose or some other, at least approximately dimensionally stable carrier material has heating means arranged in a housing to evaporate the active ingredients. A support is provided for replaceably holding an active ingredient carrier above the heating means. The active ingredient carrier is in the form of a column and is optionally inserted replaceably, with its longitudinal dimension placed vertically, in a sleeve which is adapted in its form and dimensions to the active ingredient carrier and is open at the top and bottom. The sleeve is situated inside the housing and spaced apart from the wall of the housing on all sides, said housing having exhaust gas openings at the top.

12 Claims, 2 Drawing Sheets

APPARATUS FOR THE EVAPORATION OF ACTIVE INGREDIENTS SUCH AS, FOR EXAMPLE, PYRETHRUM, INCORPORATED IN CELLULOSE OR OTHER CARRIER MATERIALS

BACKGROUND OF THE INVENTION

1. Field of the Invention

The invention relates to devices for the evaporation of active ingredients incorporated in a carrier.

2. Description of the Prior Art

In the known apparatus German Auslegeschrift No. 2,730,855, the active ingredient carrier in the form of a plate and for the purpose of evaporation of the active ingredients it is placed with its whole surface against the electric heating means which are situated behind a window in the housing and are heated to the operating temperature.

Intense evaporation of active ingredients can be achieved by this arrangement but the more intense the rate of evaporation the sooner will the reserve of active ingredients in the active ingredient plate be exhausted, with the result that the plate must be replaced after a relatively short time if a constant rate of evaporation of active ingredient over a considerable period is required.

SUMMARY OF THE INVENTION

It is an object of the present invention to improve an apparatus of the type indicated so that correctly dosed evaporation of active ingredients as required for the given circumstances can be achieved by simple means and over a much longer period of time than with known apparatus without the need to replace the active ingredient carrier.

The solution to this problem is characterised in that the active ingredient carrier is in the form of a column and optionally is inserted replaceably, with its longitudinal dimension vertically, in a sleeve which is adapted to the active ingredient carrier in its form and dimensions and is open at the top and bottom, and in that optionally the sleeve is arranged inside the housing so as to be spaced apart from the housing wall on all sides, which housing has exhaust gas openings only at the top.

Due to these measures, the surface area of active ingredient carrier facing the electric heating means and therefore exposed to the heating for evaporation of the active ingredients is relatively small compared with the volume of active ingredient carrier.

This not only ensures a well controlled rate of evaporation of active ingredients but also enables the capacity of the active ingredient carrier to be increased without any increase in the surface area of active ingredient carrier exposed to the action of the heating means.

Furthermore, the stream of air which flows upwards through the exhaust gas duct bounded by the sleeve and the wall of the housing and which has also been heated by the heating means absorbs the evaporated active ingredients by suction and carries them along at relatively high speed so that the evaporated active ingredients are uniformly distributed in the surrounding atmosphere at an hitherto unobtainable speed.

It is advantageous if the sleeve and the active ingredient carrier are situated at a vertical distance from the heating means, inter alia in order that less heat resistant and therefore less expensive materials may be used for the sleeve.

One advantageous further development of the apparatus described above consists in that the distance of the sleeve with active ingredient carrier from the heating means is adjustable.

This enables the intensity of evaporation to be altered by altering the distance of the sleeve with active ingredient carrier from the heating means, for example so that a constant rate of evaporation of active ingredient can be maintained over a prolonged period of operation.

Furthermore, for increasing the exchange of heat by convection, it is advantageous to arrange the sleeve with active ingredient carrier centrally above the heating means and to ensure that the radiant area of the heating means is greater than the area of the end face of active ingredient carrier exposed to the heating means.

One variation for selectively altering the degree of evaporation of active ingredient is characterised by electric heating means having an adjustable operating temperature.

An embodiment of the invention is described below by way of example with reference to the drawings, in which

BRIEF DESCRIPTION OF THE FIGURES

FIG. 1 represents a section taken on line I—I of FIG. 2 through an apparatus for the evaporation of active ingredients incorporated in cellulose or other carrier materials;

FIG. 2 represents the same apparatus viewed from above;

FIG. 3 represents the same in side view;

FIG. 4 represents the same viewed from below.

DESCRIPTION OF THE PREFERRED EMBODIMENT

This apparatus substantially comprises a housing 1 manufactured from dimensionally stable plastics material, with electric heating means 2 arranged inside the housing and a replaceably mounted cylindrical active ingredient carrier 3 of cellulose.

The housing 1 is an assembly composed of a base part 4 in the form of a shell, a middle part 5 arranged above the base 4 and an upper part 6. The parts 4 and 5 have an annular profile and are arranged coaxially and vertically above one another.

The wall of the middle part 5 has the same diameter as the wall of the base 4, and the upper part 6 is inserted in the middle part 5 to a depth which is limited axially and held therein by static friction.

Vent openings 7 in the form of slots are formed in the bottom of the base 4 and extend to the wall of the base 4.

The rectangular heating means are fixed between the base 4 and middle part 5 with the broad sides of the heating means 2 extending horizontally.

The electric leads 8 to the electric heating means are clamped between the adjacent edges of the housing parts 4 and 5 to relieve tension. Instead of the leads 8, the housing 1 could be equipped with two transversely extending electric plugs designed to be connected to the electric heating means 2 (plugs not shown in drawing).

The heating means 2 are fixed in position by means of vertical walls 9 extending from the bottom of the base 4 and a frame 10 formed in the middle part 5.

The said frame 10 is connected to the wall of the middle part 5 by struts. The cylindrical upper part 6 of the housing is inserted in the cylindrical housing middle part 5 above the frame 10. A coaxial sleeve 11 is formed in this upper part 6 and is continuous with the wall of the housing part 6 through radially extending walls 12.

The exhaust gas duct 13 which is bounded by the wall of the upper part 6 and the sleeve 11 is closed at the top by a grating 14 which is sufficiently dense to prevent the fingers of the hand being passed through it.

Abutments 15 in the form of intersecting transverse rods are provided at the lower opening of the sleeve 11 to limit the depth of insertion of the active ingredient carrier 3.

To facilitate adjustment of the position of the upper part 6 relative to the middle part 5, the upper part 6 carries two diametrically opposite manual adjustment devices 16 which can be pushed elastically inwards and fit into parallel vertical slots in the middle part 5 for adjustment of the height.

The maximum excursion of the upper part 6 is about 1.5 cm and the sleeve 11 with active ingredient carrier 3 is situated at a vertical distance of about 0.5 cm from the electric heating means.

The active ingredient carrier is inserted with static friction in the sleeve 11 which is closed all round its circumference. When the heating means has reached its operating temperature of about 130° C., it automatically heats the underside of the active ingredient carrier 3 to such a temperature that the active ingredients encapsulated in the carrier 3 evaporate and are carried upwards by the heated air ascending through the exhaust gas duct 13. The closer the active ingredient carrier 3 is placed to the electric heating means 2, the more intensely will the active ingredients be heated and the more rapidly will they evaporate.

The active ingredient carrier 3 having the dimensions indicated, with a diameter of about 2 cm and an axial length of about 3 cm or more and containing about 4.5 g of active ingredient is capable of providing a constant rate of evaporation of active ingredient over a period of about 8 days, during which the carrier 3 should initially be placed at a considerable distance from the electric heating means and should then be moved progressively closer to the heating means as evaporation continues.

The rate of outflow of heated air and hence also of evaporated active ingredients may be increased by conically constricting the exhaust gas duct 13 in the upward direction. Instead of or in addition to adjustment of the height of the active ingredient carrier to alter the degree of evaporation, heating means with a variable operating temperature may be provided, but this is not only considerably more expensive than a heating means which has a constant operating temperature but is also liable to jeopardize the function of the apparatus if the operating temperature rises above 130° C.

It may in some circumstances be advantageous to mount several active ingredient carriers according to the invention above a common heating means.

All novel individual features and combination features disclosed in the description and/or drawing are regarded as essential to the invention.

In a preferred embodiment of the apparatus, the cylindrical container 3 is provided for receiving the preferably porous active ingredient carrier and is closed from the heating plate 2 by a base. If the container 3 is made of metal or some other thermally highly conductive material, the heat radiated from the heating plate 2 acts on all sections of the wall and base of the container 3 and results in intensive but uniform evaporation of the active ingredients.

According to another embodiment, the sleeve 11 holding the cylindrical container 3 has openings arranged at intervals, i.e. distributed over its circumference, so that the hot air from the heating plate 2 can act through these openings on the cylindrical container 3 which is made, for example, of a thermally highly conductive material, and the container 3 is thereby heated substantially uniformly over its whole length or height. The active ingredients can thereby be evaporated even at lower temperatures.

What is claimed is:

1. Apparatus for evaporating active ingredients in an ingredient carrier comprising:

a housing defined by first and second, generally tubular, coaxial parts in mutual end-to-end engagement wherein at least a portion of the first part is adapted to fit within the second part;

the first part including a peripheral wall, a generally axially oriented tubular sleeve, having a lower end adjacent the second housing part, adapted to hold within the sleeve the active ingredient carrier so that an end face of the carrier is proximate an end of the sleeve, and means connecting the sleeve to the peripheral wall to define therebetween a duct extending from the one end of the first part to the other end thereof;

the second part defining a base adapted to support the housing on a support surface and including means for flowing air to the one end of the duct and means operatively engaging the first part permitting relative axial movements between the parts, the second part further including a peripheral wall surrounding the peripheral wall of the first part, and including at least one opening through which a portion of the peripheral wall of the first part is exposed, the opening being of a sufficient size so that it can be touched with a finger to facilitate relative axial movement between the first and second parts by touching the peripheral wall of the first part and forcing it inwardly; and heating means carried by the second part in generally alignment with the sleeve and situated opposite and generally beneath and the lower end thereof for heating the active ingredient carrier in the tubular sleeve;

whereby air heated by the heating means flows through the duct and the end of the first part to the exterior of the housing and the evaporated active ingredients released by the carrier are entrained in the air flow; and whereby the rate of active ingredient evaporation can be varied by changing the relative axial positions of the first and second parts to correspondingly change the distance between the heating means and the end face of the carrier in the tubular sleeve.

2. Apparatus according to claim 1, wherein the sleeve and the active ingredient carrier are placed a chosen vertical distance from the heating means.

3. Apparatus according to claim 1, wherein the sleeve and the active ingredient carrier are placed centrally above the heating means, and wherein the heating means includes a radiant surface which is larger than the surface area of the carrier end face.

4. Apparatus according to claim 1, wherein the sleeve and active ingredient carrier are placed centrally within the housing.

5. Apparatus according to claim 1, wherein the sleeve and the peripheral wall have an annular profile and are arranged coaxially.

6. Apparatus according to claim 1, wherein the sleeve and the active ingredient carrier are each uniform in cross-section over their entire length.

7. Apparatus according to claim 1, wherein the internal cross-section of the first part is greater at the one end than at the other end.

8. Apparatus according to claim 1, including a grating covering the duct.

9. Apparatus according to claim 1, including a lid covering the end of the sleeve adjacent the other end of the first part.

10. Apparatus according to claim 1, including inwardly projecting abutments at the end of the sleeve proximate the one end of the first part for limiting the depth of insertion of the active ingredient carrier.

11. Apparatus for the evaporation of active ingredients in an ingredient carrier comprising:

a housing having a base part, a middle part and an upper part, the base part including a top, a side and a bottom, and at least one ventilation opening, the bottom including a generally centrally located support wall extending vertically upward, the middle part including a top, a side and a generally centrally located frame disposed in a generally horizontal plane within the middle part, and struts connecting the frame to the side of the middle part, the middle part being coaxially connected to the top of the base part, and being adapted to receive the upper part, the upper part including a side, a top, a tubular sleeve having exterior and interior vertical surfaces, radially extending walls connecting the sleeve to the side, the sleeve and the side defining between them an exhaust gas duct; a grating at the top of the upper part permitting the passage of gases from the duct to the exterior of the housing, the sleeve generally extending over substantially the full length of the upper part and terminating in a sleeve opening which is proximate the middle part, and abutment rods extending across the sleeve opening;

means coaxially positioning and frictionally connecting the upper part to the middle part, and permitting relative axial movement between them;

an ingredient carrier adapted to be placed inside the sleeve and having an end face to engage and be supported by the abutment rods;

electric heating means disposed on the frame and supported by the support wall in the base part so that heat from the heating means rises upwardly towards the sleeve and the exhaust gas duct;

whereby upon activation, the heating means heats the ingredient carrier to release the active ingredients therein, and the rate of release can be controlled by slidably moving the upper housing part within the middle housing part to vary the spacing between the end face of the ingredient carrier and the heating means.

12. Apparatus for evaporating active ingredients in an ingredient carrier comprising:

a housing defined by first and second, generally tubular, coaxial parts in mutual end-to-end engagement wherein at least a portion of the first part is adapted to fit within the second part;

the first part including a peripheral wall, a generally axially oriented tubular sleeve, having a lower end adjacent the second housing part, adapted to hold within the sleeve the active ingredient carrier so that an end face of the carrier is proximate an end of the sleeve, the sleeve and active ingredient panel being placed centrally within the housing and situated centrally above a heating means, and means connecting the sleeve to the peripheral wall to define therebetween a duct extending from the one end of the first part to the other end thereof;

the second part defining a base adapted to support the housing on a support surface and including means for flowing air to the one end of the duct and means operatively engaging the first part permitting relative axial movements between the parts, the second part further including a peripheral wall surrounding the peripheral wall of the first part, and including at least one opening through which a portion of the peripheral wall of the first part is exposed, the opening being of a sufficient size so that it can be touched with a finger to facilitate relative axial movement between the first and second parts by touching the peripheral wall of the first part and forcing it inwardly; and heating means, including a radiant surface which is larger than the surface area of the carrier end face, carried by the second part in generally alignment with the sleeve and situated opposite and generally beneath the lower end thereof for heating the active ingredient carrier in the tubular sleeve;

whereby air heated by the heating means flows through the duct and the end of the first part to the exterior of the housing and the evaporated active ingredients released by the carrier are entrained in the air flow; and whereby the rate of active ingredient evaporation can be varied by changing the relative axial positions of the first and second parts to correspondingly change the distance between the heating means and the end face of the carrier in the tubular sleeve.

* * * * *